United States Patent [19]

Terao et al.

[11] Patent Number: 4,826,872

[45] Date of Patent: May 2, 1989

[54] PHARMACEUTICAL COMPOSITION FOR TREATMENT OF CATARACT

[75] Inventors: Shinji Terao, Osaka; Mitsuyoshi Azuma, Hyogo; Noriko Watanabe, Osaka, all of Japan

[73] Assignee: Takeda Chemical Industries, Ltd., Japan

[21] Appl. No.: 121,919

[22] Filed: Nov. 17, 1987

[30] Foreign Application Priority Data

Dec. 3, 1986 [JP] Japan .................................. 61-288076

[51] Int. Cl.$^4$ .............................................. A61K 31/27
[52] U.S. Cl. ...................... 514/474; 514/912
[58] Field of Search ................. 514/474, 912; 549/315

[56] References Cited

FOREIGN PATENT DOCUMENTS 146121 6/1985 European Pat. Off. ............ 549/315
189272 7/1986 European Pat. Off. ............ 514/912
202589 11/1986 European Pat. Off. .

OTHER PUBLICATIONS

Chem. Abst.: 106:176,797m, (1987), Terao et al.
Chem. Abst.: 106:214301e, (1987), Terao et al.
Chem. Abst.: 108:118735v, (1988), Motoi.
Chem. Abst.: 108:150,870w, (1988), Kato et al.
Duncan, George, "*Mechanisms of Cataract Formation in the Human Lens*", 1981.
Bhuyan Kailash C. and Bhuyan, Durga K., "*Molecular Mechanism of Cataractogenesis: III. Toxic Metabolites of Oxygen as Initiators of Lipid Peroxidation and Cataract*", Current Eye Research, vol. 3, No. 1, 1984.

*Primary Examiner*—Douglas W. Robinson
*Attorney, Agent, or Firm*—Wegner & Bretschneider

[57] ABSTRACT

The present invention relates to a treatment of cataract by administering a compound of the formula:

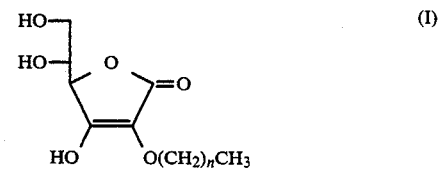

wherein n is an integer of 8 to 20, and use thereof.

The compound (I) of this invention has an excellent therapeutic effect against various types of cataract.

10 Claims, 1 Drawing Sheet

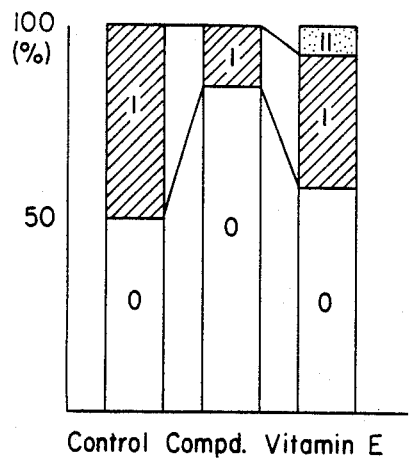
FIG. I(I-A) 2 Weeks
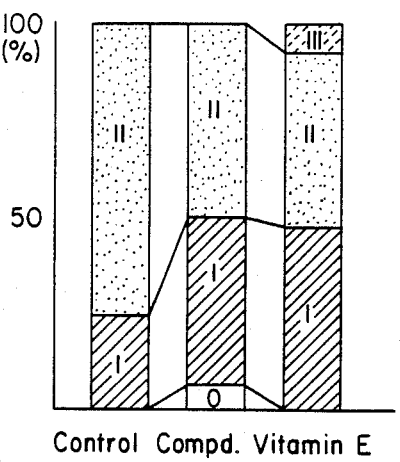
FIG. I(I-B) 3 Weeks
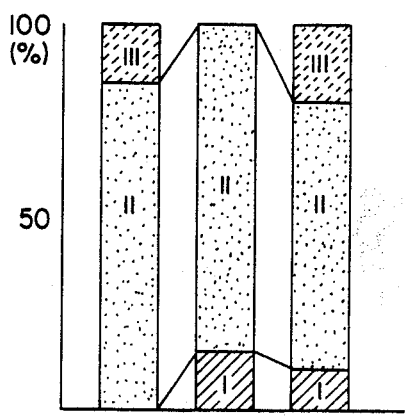
FIG. I(I-C) 4 Weeks
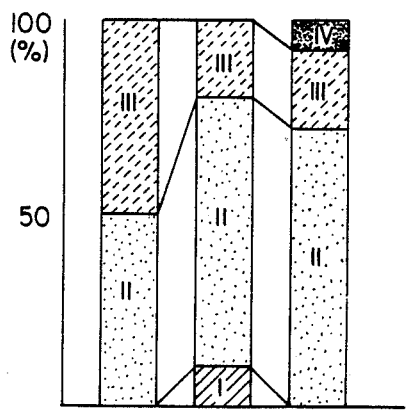
FIG. I(I-D) 5 Weeks

PHARMACEUTICAL COMPOSITION FOR TREATMENT OF CATARACT

This invention relates to a pharmaceutical composition for treatment of cataract.

Cataract is an eye disease due to opacity of the crystalline lens; reduced transparency of the lens will obstruct a sufficient amount of light from reaching the eyeground, which results in diminished visual acuity.

Cataract is classified pathogenically into congenital cataract (cataracta stationaris), senile cataract (cataracta senilis), complicated cataract (cataracta complicata), traumatic cataract (cataracta traumatica), diabetic cataract (cataracta diabetica), etc., and in addition irradiation cataract and glassworker's cataract are also known. All of them are accompanied by diminished visual acuity, are serious eye diseases.

Although the detailed pathogenesis of cataract still remains unknown, lipid peroxidation has been suggested to be involved in it. Adriamycin and streptozocin which are said to be converted into radicals in organisms, and amizole, a specific inhibitor of catalase, have been found to induce cataract [Mechanism of Cataract Formation in the Human Lens; G. Duncan ed., Academic Press, New York, pp.117-150 (1981)]. Increased level of peroxidized fat in the lens has also been demonstrated in human subjects suffering from cararact [Current Eye Res., 3, 67-81 (1984)]. Thus radical molecules and active oxygen species (for example, superoxide, hydrogen peroxide, hydroxide radical) have been demonstrated to be involved in induction of cataract, even if there remain many unclarified details and a practical treatment of cataract based on these mechanisms is a long way off.

Therefore it may be said that the current treatment of cataract is practically limited to surgical procedures. Surgical procedures include a procedure to move the lens within the eyeball, and a procedure to extirpate the whole lens out of the eyeball, which are accompanied necessarily with incision and ligation of the cornea and an operative wound in the lens, which impose a burden upon patients notwithstanding the recent progress in surgical techniques.

Medicinal treatment, if any, would be the best but is considered impossible even today because of the very slow metabolism in the lens.

Instillation of glutathione was said to be effective to some extent for treatment of cataract, but many specialists are doubtful of its effectiveness.

The inventors synthesized derivatives of ascorbic acid by introducing a substituent at the hydroxyl group on the 2-position of the acid molecule, and established the usefulness of the derivatives as antioxidants [EP Publication (laid open)No. 0146121]. Later the inventors found the circulatory system-improving effects of said derivatives of ascorbic acid, such as antiarrhythmia, antimyocardial infarction, anticerebral infarction, and prevention of presbyophrenia, by means of the free radical scavenging effect of the said derivatives [EP Publication (laid open) No. 0202589].

As a result of further researches, the inventors have found a therapeutic effect for cataract of some derivatives of ascorbic acid, and they investigated also the bioavailability of the derivatives and pharmaceutical preparations containing the derivatives, to complete the present invention.

Thus, this invention provides a pharmaceutical composition for treatment of cataract containing a compound of the formula:

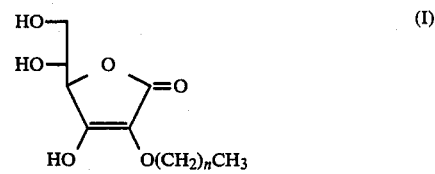

wherein n represents an integer of 8 to 20.

In the formula of the compound described above, the integer represented by n is preferably an integer of 9 to 18 and particularly of 9 to 17 to make straight-chain alkyls are most desirable. The compounds may be D-isomers or L-isomers, and L-isomers are preferable.

Methods of production and physical and chemical properties of the compound (I) are described in detail in the EP Publication (laid open) No. 0146121 cited above.

The compound (I), when used as a remedy for cataract, can usually be administered orally or parenterally in the form of pharmaceutical compositions (e.g. tablets, capsules, eye-drops or eye ointment), produced according to per se known methods by mixing with a per se known pharmaceutically acceptable additives such as carrier, excipient or diluent.

For examples, in the case of eye-drops, a compound (I) of about 0.001-3%(W/V), preferably about 0.01-1%(W/V), is added to a basal medium to make an aqueous solution or a suspension. The pH of the eye-drops of this invention is adjusted to about 4-10, preferably about 5-9. The eye-drops of the present invention may be sterilized so as to make the final product sterile. The sterilization may be conducted at any step of preparing the eye-drops. For administration, one to a few drops per dose is instilled in the eye with a frequency of 1 to about 4 times a day according to the patient's condition. Such eye-drops may further contain pharmaceutically acceptable additives such as buffers for pH adjustment, e.g. phosphate buffer, borate buffer, citrate buffer, tartrate buffer and acetate buffer; isotonizing agents, e.g. sorbitol, glycerol, polyethylene glycol, propylene glycol, glucose and sodium chloride; preservatives, e.g. benzalkonium chloride, parahydroxybenzoic acid esters, benzyl alcohol, parachloro-metaxylenol, chlorocresol, phenethyl alcohol, sorbic acid, sorbic acid salts, thimerosal and chlorobutanol; chelating agents, e.g. edetate sodium and condensed sodium phosphate; and thickening agents, e.g. carboxypropylcellulose, hydroxyethylcellulose, hydroxypropylcellulose, polyvinylalcohol and sodium polyacrylate.

An eye ointment is produced by admixing the active ingredient in a concentration of about 0.001-3%(W/V), preferably 0.01-1%(W/V), with a conventional eye ointment base. When preparing the eye ointment of the present invention, procedures for pulverization of compound (I) and sterilization of the composition are preferable. The eye ointment is administered 1 to about 4 times a day depending on the patient's condition. As the eye ointment base, there may be mentioned petrolatum, Macrogol and carboxymethylcellulose, among others.

For oral administration, the daily dose of tablets and capsules for an adult is usually 50 mg to 500 mg, preferably 100-250 mg. For examples, tablets are usually prepared by the following procedures. The compound (I) is first rendered granular with or without uniform admixture with a diluent (e.g. lactose), binder (e.g. syrup, gum arabic, gelatin, sorbitol, tragacanth, polyvinylpyrrolidone), disintegrator (e.g. potato starch), and other suitable additives. The resultant granules are provided with additives such as a lubricant (e.g. magnesium stearate, talc, polyethyleneglycol, silica), and compressed into a desired shape and size. These granules are usually prepared by compressing the compound (I) or the above mixtures and crushing to granules, or by adding moistening agent (e.g. sodium lauryl sulfate) to the compound (I) or the above mixture, granulating and drying.

In each dosage form, the composition of the present invention may contain any other pharmacologically active ingredients unless they are unsuited for the purpose of the present invention.

The toxicity of the compound (I) is low, as, for example, in an acute toxicity test in mice, no death was found even after the oral dose of 1,000 mg/kg.

The compound (I) is therapeutically effective, i.e. cataract-controlling against various types of cataract such as congenital cataract, senile cataract, complicated cataract, traumatic cataract, and diabetic cataract, being particularly remarkably effective against diabetic cataract.

Bioavailability of the compound (I) in the eye region is high, and the compound (I) has excellent biological properties different from those of the compounds known only to scavenge radicals, as shown in the experiments described below.

BRIEF DESCRIPTION OF THE DRAWINGS

FIG. 1 shows the course of the progress of cataract in the experimental animals, wherein 0–IV represent the stages of the progress, and the ordinate represents the percentage (%) of the animals at each stage.

EXPERIMENT 1

Test procedure: 4-week-old male S.D. strain rats were purchased from Shizuoka Prefecture Animals Farmers' Cooperative, grouped by 10 animals after 5 days of preliminary feeding, and subjected to the test. These rats were given a 3.5% solution of streptozocin (manufactured by Sigma Co.) in 0.002 M citrate buffer (pH 4.5) at the dose of 70 mg/kg via the caudal vein. To 2-0-octadecylascorbic acid [n=17; compound (I-A)]group, a 2.5% suspension of the compound from the day of streptozocin administration, and a 1% suspension of the compound from 3 days after streptozocin administration were orally given at 9:00 a.m. and 6:00 p.m. at the dose of 200 $\mu$l/100 g body weight (that is, 100 mg/kg/day on the first two days and 40 mg/kg/day from 3 days after on), though on the day of streptozocin administration the suspension was given 1 hour after the administration and at 6:00 p.m. To the vitamin E group, tocopherol acetate (50 mg/ml) was given orally in the same way at the dose of 400 $\mu$l/100 g (400 mg/kg/day). To the control group, tap water was orally given at 200 $\mu$l/100 g. Observation of the lens: 7, 14, 21, 28 and 35 days after streptozocin administration, the lens was observed with a slit lamp (SL-5D), and evaluated by classifying into 7 stages up to the stage of mature cataract according to the method of Sasaki et al. [Ophthalmic Res., 15, 185 (1983)].

0 No opacity is observed in the lens.
I The surface of the lens is slightly opaque or small vacuoles appear on the equator.
II Vacuoles increase in number and distribute over the cortex while fusing with each other.
III Vacuoles distributed over the most part of the cortex begin to disappear.
IV Most vacuoles have disappeared, and the whole cortex becomes opaque and translucent.
V The nucleoplasm becomes opaque.
VI The whole lens becomes white turbid.

Results:

Observation of the lens with a slit lamp revealed that in the control group, opacity was found 7 days after streptozocin administration in an eye, 14 days after the administration in 50% of the lenses (Stage I), and 21 days after in all lenses; 35 days after the administration, the lenses of Stage II and those of Stage III accounted for 50% each. On the other hand, in the Compound (I-A) group, cataract progressed more slowly than in the control group; according to the statistical analysis of the difference between the two groups (Kruskal-Wallis H-test), the compound (I-A) delayed significantly the progress of cataract. However, the vitamin E group followed a similar course to that of the control group, and thus vitamin E did not delay the progress of cataract (FIG. 1).

EXPERIMENT 2

The inhibitory effect of 2-0-octadecylascorbic acid [compound (I-A)]on lens epithelial cells was studied.

DL-$\alpha$-tocopherol, an antioxidant, was used as the reference substance.

The method of culture of rabbit lens epithelial cells

The lens epithelial cells were obtained from a male white rabbit weighing about 2 kg. Thus, after the rat was sacrificed, the eyeballs were immediately enucleated and subjected to the following aseptic procedures. The eyeballs were washed with Hank's balanced salt solution (pH 7.2), disinfected by 30-second immersion in 80% alcohol and re-washed with the same balanced salt solution. Then, using a small knife, the sclera was cut open from the posterior part of the bulb and the lens was taken out. The retina, vitreous body and the zonule of Zinn were removed. Then, the capsule was punctured and separated from the lens by means of forceps. (The epithelial cells came off with the capsule). The separated capsule was incubated in 0.01% EDTA-0.125% trypsin at 37° C. for 20 minutes After addition of the culture medium mentioned below, the mixture was centrifuged at 1,000 rpm for 2 minutes. By repeating this procedure, the epithelial cells were isolated. These cells were subjected to a few serial passages and used in the experiment. The culture medium was Eagle's medium (MEM) supplemented with 15% bovine fetal serum.

The following two oxidation systems were used in the experiment: the system using the cytotoxic effect of lipid peroxidation products produced by auto-oxidation of docosahexaenoic acid as an indicator and the system using the cytotoxic effect of activated oxygen species produced by the xanthine-xanthine oxidase system as an indicator. Thus, the confluent cells in dishes were incubated in the following media for 24 hours and the lipid peroxides in the cultures were determined.

| Test System I | |
| --- | --- |
| (1) Normal: | Cultured in MEM only |
| (2) Control: | Cultured in MEM supplemented with 250 $\mu$g/ml of docosahexaenoic acid |

-continued

| Test System I | |
|---|---|
| (3) Drug: | Cultured in MEM supplemented with 250 μg/ml of docosahexaenoic acid plus the drug. |

| Test System II | |
|---|---|
| (1) Normal: | Cultured in MEM only |
| (2) Control: | Cultured in MEM supplemented with 1 mM of xanthine and 0.01 U/ml of xanthine oxidase |
| (3) Drug: | Cultured in MEM supplemented with 1 mM of xanthine and 0.01 U/ml of xanthine oxidase plus the drug. |

Determination of peroxylipids

The thiobarbituric acid method of Yagi [Anal. Biochem., 95, 351–358 (1979)] was used for Test System I and the method of Nakashima [Chem. Pharm. Bull., 33. 5380–5384 (1985)] and Ohsawa [Anal. Sci., 1, 473–476 (1985)] using 1,3-diphenyl-2-thiobarbituric acid was employed with some modification for Test System II.

Results In Test System I, the inhibitory effect of compound (I-A) on the impairment of lens epithelial cells by the lipid peroxidation products formed by auto-oxidation of docosahexaenoic acid was investigated. As a result, compound (I-A) was found to strongly inhibit the formation of MDA (Malondialdehyde) at low concentrations ($<5$ μg/ml) but its inhibitory effect was attenuated at higher concentrations. DL-α-tocopherol showed the same effect at about 50 times as high a concentration as compound (I-A) (Table 1).

In Test System II, the inhibitory effect of compound (I-A) on the impairment of lens epithelial cells by the activated oxygen species produced by the xanthine-xanthine oxidase system was investigated. As a result, compound (I-A) was found to be as effective as DL-α-tocopherol, causing a substantially complete inhibition of MDA (Table 2).

TABLE 1

| Amount of MDA in culture medium (Test System I) | |
|---|---|
| Drug | MDA (n mole/ml) |
| normal | 1.5 ± 0.2 |
| Control | 29.2 ± 3.9 |
| Compound (I-A) (2.5 μg/ml) | 6.5 ± 0.1 |
| Compound (I-A) (5 μg/ml) | 5.8 ± 0.7 |
| Compound (I-A) (10 μg/ml) | 10.3 ± 0.6 |
| DL-α-Tocopherol (125 μg/ml) | 4.2 ± 0.1 |

TABLE 2

| Amount of MDA in culture medium (Test System II) | |
|---|---|
| Drug | MDA (n mole/ml) |
| Normal | 0.005 ± 0.008 |
| Control | 0.134 ± 0.037 |
| Compound (I-A) (2 μg/ml) | 0.024 ± 0.015 |
| Compound (I-A) (10 μg/ml) | 0.016 ± 0.014 |
| Compound (I-A) (50 μg/ml) | 0.001 ± 0.001 |
| DL-α-Tocopherol (10 μg/ml) | 0.009 ± 0.011 |

| Example 1 Ophthalmic suspension (eye-drops) | (W/V) % |
|---|---|
| 2-O—octadecylascorbic acid | 1.0 |
| polyvinyl alcohol | 0.5 |
| dibasic sodium phosphate (dodecahydrate) | 0.5 |
| monobasic sodium phosphate (dihydrate) | 0.2 |
| disodium edetate | 0.02 |
| sodium chloride | 0.7 |
| benzalkonium chloride | 0.007 |
| sterile purified water ad. | 100.0 |

To about 800 ml of sterile purified water are dissolved 5 g of olyvinyl alcohol, 5 g of dibasic sodium phosphate, 0.2 g of disodium edetate and 7 g of sodium chloride. After sterilizing the solution by filtration, 10 g of 2-o-octadecylascorbic acid and 0.07 g of benzalkonium chloride are added to the above obtained solution under sterile conditions. The mixture is thoroughly agitated to make the total 1000 ml. Thus obtained suspension is filled into bottles to make an ophthalmic suspension.

| Example 2 Ophthalmic solution (eye-drops) | (W/V) % |
|---|---|
| 2-O—decylascorbic acid | 0.1 |
| boric acid | 1.7 |
| sodium borate | 0.4 |
| sodium edetate | 0.02 |
| benzalkonium chloride | 0.005 |
| sterile purified water ad. | 100.0 |

To 800 ml of sterile purified water are dissolved 17 g of boric acid, 4 g of sodium borate, 0.2 g of sodium edetate and 0.05 g of benzalkonium chloride. To the thus obtained solution is added 1 g of 2-octadecyl-ascorbic acid to make a solution. Then, to this solution is further added sterile purified water to make the total volume 1000 ml. After sterilizing the solution by filtration the solution is filled into bottles to obtain an ophthalmic solution

| Example 3 Tablet | |
|---|---|
| 2-O—octadecylascorbic acid | 50 mg |
| corn starch | 90 mg |
| lactose | 25 mg |
| hydroxypropylcellulose L | 25 mg |
| magnesium stearate | 5 mg |
| total | 200 mg (per tablet) |

50 g of 2-O-octadecylascorbic acid is first rendered granular with 90 g corn starch, 25 g of lactose and 25 g of hydroxypropylcellulose L. The resultant granules are provided with 5 g of magnesium stearate and compressed into tablets.

| Example 4 Eye ointment | (W/W) % |
|---|---|
| 2-O—decylascorbic acid | 0.5 |
| liquid paraffin | 1.0 |
| white petrolatum ad. | 100.0 |

Under sterile conditions, 1 g of sterilized liquid paraffin and 0.5 g of 2-O-decylascorbic acid are poured into a mortar, then are kneaded (pulerized) thoroughly. To the mixture, white petrolatum is gradually added under kneading to make total weight 100 g. Thus obtained product is filled in a tube for ophthalmic use to obtain an eye ointment.

What is claimed is:

1. A method for treatment of a cataract, which comprises administering to a mammal suffering therefrom a therapeutically effective cataract retarding amount of a compound of the formula:

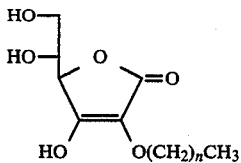

wherein n is an integer of 8 to 20, in the form of a tablet, a capsule, eyedrops or an eye ointment.

2. The method according to claim 1, wherein n is an integer of 9 to 18.

3. The method according to claim 2, wherein n is an integer of 9 to 17 to form a straight-chain alkyl.

4. The method according to claim 3, wherein n is 9.

5. The method according to claim 3, wherein n is 17.

6. The method according to claim 1, wherein the compound is administered in the form of eye-drops.

7. The method according to claim 6, wherein the eye-drops contains the compound in an amount of about 0.001 to 3% (W/V).

8. The method according to claim 6, wherein the eye-drops further contains preservative.

9. The method according to claim 6, wherein the eye-drops are in the form of an aqueous solution.

10. The method according to claim 6, wherein the eye-drops are in the form of an aqueous suspension.

* * * * *

UNITED STATES PATENT AND TRADEMARK OFFICE
CERTIFICATE OF CORRECTION

PATENT NO. : 4,826,872

DATED : May 2, 1989

INVENTOR(S) : Shinji TERAO et al.

It is certified that error appears in the above-identified patent and that said Letters Patent is hereby corrected as shown below:

On cover page of patent, Item [73], after "Japan"

add --and Senju Pharmaceutical Co., Ltd., Japan--.

Signed and Sealed this

Eighth Day of January, 1991

Attest:

HARRY F. MANBECK, JR.

*Attesting Officer*  *Commissioner of Patents and Trademarks*